(12) United States Patent
Mikaelian

(10) Patent No.: US 8,097,284 B2
(45) Date of Patent: Jan. 17, 2012

(54) POLARIZED SCORPION VENOM SOLUTION AND A METHOD FOR MAKING POLARIZED SCORPION VENOM SOLUTION

(76) Inventor: Arthur Mikaelian, Beverly Hills, CA (US)

( * ) Notice: Subject to any disclaimer, the term of this patent is extended or adjusted under 35 U.S.C. 154(b) by 179 days.

(21) Appl. No.: 12/270,664

(22) Filed: Nov. 13, 2008

(65) Prior Publication Data

US 2009/0123558 A1     May 14, 2009

Related U.S. Application Data

(60) Provisional application No. 60/987,756, filed on Nov. 13, 2007.

(51) Int. Cl.
*A61K 35/24* (2006.01)
*C12N 9/00* (2006.01)
*C07K 1/00* (2006.01)
*C07H 21/04* (2006.01)

(52) U.S. Cl. ....... 424/537; 435/183; 530/350; 536/23.1; 536/23.2

(58) Field of Classification Search ........................ None
See application file for complete search history.

(56) References Cited

U.S. PATENT DOCUMENTS

| | | | |
|---|---|---|---|
| 6,319,891 | B1 | 11/2001 | Sontheimer |
| 6,429,187 | B1 | 8/2002 | Sontheimer |
| 6,667,156 | B2 | 12/2003 | Sontheimer et al. |
| 6,870,029 | B2 | 3/2005 | Sontheimer |
| 2006/0252676 | A1 | 11/2006 | Zhang et al. |
| 2007/0237714 | A1 | 10/2007 | Alvarez |

OTHER PUBLICATIONS

Yan et al. Peptides. Oct. 12, 2010.*
Bordier C. M., Martinez F. M. M., Salgado S. H. L., Bory P. G. H., Perry B. F., Granado M. R. et al. Composicion antitumoral. Certificado de autor de invencion 1995; #AGIK 35/56.
Castenada Pasaton O. Toxinas animales: Acciones facilitadoras de la transmisión colinérgica. Revista Biologia 2000; 14(1): 1-15.
Compton MM. A biochemical hallmark of apoptosis: internucleosomal degradation of the genome. Cancer Metastasis Rev Sep. 1992; 11(2):105-19.
Chen, B. and Ji, Y. Antihyperalgesia effect of BmK AS, a scorpion toxin, in rat by plantar injection. Brain Res. 2002; 952 2, pp. 322-326.
De Armas LF. Escorpiones del Archipiélago Cubano. IV. Nueva Especie de Rhopalurus (Scorpionida: Buthidae). Poeyana 1974; 136:1-12.
Dint L, Coppola S, Ruzittu MT, Ghibelli L. Multiple pathways for apoptotic nuclear fragmentation. Exp Cell Res Mar. 15, 1996; 223(2):340-7.
Guan, R.J., Wang, C.G., Wand, M. and Wang, D.C. A depressant insect toxin with a novel analgesic effect from scorpion *Buthus martensii* Karsch. Biochim. Biophys. Acta 2001; 1549 1, pp. 9-18.
Guan, R.J., Wang, M., Wang, D. and Wang, D.C. A new insect neurotoxin AngP1 with analgesic effect from the scorpion *Buthus martensi* Karsch: purification and characterization. J. Pept. Res. 2001;58 10, pp. 27-35.
Kourie, J.I., Shorthouse, A.A., Properties of cytotoxic peptide-formed ion channels. Am J Physiol Cell Physiol 2000; 278: 1063-1087.
Liu, Y.F., MA, R.L., Wang, S.L., Duan, Z.Y., Zhang, J.H., Wu L.J. and Wu, C.F. Expression of an antitumor-analgesic peptide from the venom of Chinese scorpion *Buthus martensi* Karsch in *Escherichia coli*. Protein Expr Purif. 2003; 27 2, pp. 253-258.
Omran, M A. Cytotoxic and apoptotic effects of scorpion *Leiurus quinquestriatus* venom on 293T and C2C12 eukaryotic cell lines. J Venom Anim Toxins incl Trop Dis 2003; 9(2):255-76.
Rajendra, W., Arunmozhiarasi, A., Jeyaseelan, K. Toxins in antinociception and anti-inflammation. Toxicon; 2004 44 1, pp. 1-17.
Xiong, Y.M., Lan, Z.D., Wang, M., Liu, B., Liu, X.Q. Molecular characterization of a new insect neurotoxin with an analgesic effect on mice from the scorpion *Buthus martensi* Karsch. Toxicon 1999;37 8, pp. 1165-1180.

* cited by examiner

*Primary Examiner* — Christian Fronda
(74) *Attorney, Agent, or Firm* — Marc E. Hankin; Kevin Schraven; Hankin Patent Law, APC

(57) ABSTRACT

Various embodiments of this invention disclose a polarized dilute blue scorpion venom solution, a method for making a polarized dilute scorpion venom solution, and a method for administering dilute scorpion venom solution. The polarized dilute scorpion venom solution relieves pain, improves immune-system response, treats cancer, prevents cancer, improves quality of sleep, reduces inflammation, and minimizes negative biological response to chemotherapy and radiation treatment.

1 Claim, 9 Drawing Sheets

POLARIZED SCORPION VENOM SOLUTION AND A METHOD FOR MAKING POLARIZED SCORPION VENOM SOLUTION

Priority is claimed to U.S. Provisional Patent Application Ser. No. 60/987,756, filed on Nov. 13, 2007, and titled "Analgesic, Antiinflammatory, Immunity Boosting, Antitumoral, and Cancer Preventing and Treating Methodology Using Organic, Modified, and Magnetically Polarized Scorpion Venom and Synthetics Thereof." This priority application is incorporated by reference herein as though set forth herein in full.

BACKGROUND OF THE INVENTION

This invention generally relates to analgesic and anti-tumor solutions. Specifically, it pertains to a polarized dilute scorpion venom solution, a method for making a polarized dilute scorpion venom solution, and a method for administering dilute scorpion venom solution. The polarized dilute scorpion venom solution relieves pain, improves immune-system response, treats cancer, prevents cancer, improves quality of sleep, reduces inflammation, and minimizes negative biological response to chemotherapy and radiation treatment.

Around the world, research is being done on the potential effectiveness of scorpion venom as a cancer-fighting tool. Scientists have taken a synthetic version of venom of *Leiurus quinquestriatus*, also known as the Giant Yellow Israeli scorpion, labeled it with radioactive iodine and found it to be an effective delivery vehicle for targeted radiotherapy against glioma. The synthetic venom binds to glioma cells and has an unusual ability to pass through the blood-brain barrier that blocks most substances from reaching brain tissue from the bloodstream. The synthetic venom is used primarily as a carrier to transport radioactive iodine to glioma cells, but there is data that suggests that it may also slow down the growth of tumor cells.

Dr. M. A. A. Omran of Suez Canal University in Egypt published the study "Cytotoxic and apoptotic effects of scorpion *Leiurus quinquestriatus* venom on 293T and C2C12 eukaryotic cell lines" in the Journal of Venomous Animals and Toxins including Tropical Diseases. Dr. Omran's study proves the venom from scorpions of the Buthidae family, particularly *Leiurus quinquestriatus*, produces apoptosis in human cells. The most intriguing element of Dr. Omran's study was that it showed that scorpion venom produces both apoptosis (cellular suicide) and necrosis (cellular death through trauma). The key issue is concentration. At certain concentrations, scorpion venom resulted in apoptosis. In other, larger concentrations, cytotoxicity shifted to necrosis.

Like *Leiurus quinquestriatus*, *Rhopalurus junceus* (blue scorpion) belongs to the Buthidae family of scorpions. The blue scorpion is indigenous to Eastern Cuba, Venezuela, Haiti, and the Dominican Republic. Blue scorpion venom, has been used as a folk medicine in Eastern Cuba for generations. It was found that in a certain areas of Cuba when people who had chronic conditions were stung by the blue scorpion, their conditions surprisingly improved instead of getting worse. In 1980, blue scorpion venom was researched in the Cuban province of Guantanamo, one of the areas where the blue scorpion is indigenous. Originally the chemicals taken from the blue scorpion were used primarily to treat ailments in animals. The effects upon animals were found to be extraordinary. Doctors then began to consider the positive impact it could have upon the health of humans. In the early 1990's, blue scorpion venom was tested on a human patient and was found to shrink, and then eliminate, the tumor of a young Cuban woman. Ever since that event it has been in use as an aggressive treatment for anti-tumor therapy.

Recently, blue scorpion venom has been shown to have a variety of health benefits including powerful analgesic and anti-inflammatory effects. In addition to cancer, blue scorpion venom has been shown to have positive results with a wide variety of immune-system related diseases including: HIV; Alzheimer's Disease; Multiple Sclerosis; Muscular Dystrophy; and Arthritis. During the last 15 years, over 60,000 people outside the United States have taken blue scorpion venom and witnessed great improvements in their lives.

Although blue scorpion venom has been used in the past to treat pain, inflammation, cancer, and other ailments the delivery systems and scorpion venom solutions themselves have been inconsistent. This made administration of an effective blue scorpion venom solution difficult. Thus, there is a need in the art for a blue scorpion venom solution that is stable, safe, effective, and consistent.

Moreover, blue scorpion venom, like many liquids, is most effective when it is polarized.

A polarized liquid, as compared to non-polarized liquid, is absorbed far more rapidly into the human body and is significantly more bio-available on a cellular level, resulting in significantly improved results. This has been tested in small scale blind studies in which the cases did not know whether or not they were receiving unpolarized liquid or polarized liquid. In those cases where individuals actually received polarized/magnetized liquid, they reported significantly improved results over those individuals who received non-polarized liquid. It is believed that the effects of the polarization process stays effectively within the liquid for three to four weeks before the liquid returns to a state similar to pre-polarization. To polarize scorpion venom, the venom is repeatedly exposed to fixed magnetic fields aligns the magnetic poles of the molecules within the scorpion venom liquid in such a way that it forms a geometric consistency between the molecules which influences the body's ability to recognize the liquid and open molecular gates for better absorption. This process preferably utilizes fixed magnets; however, electromagnets may also be used. This process is an integral part of the solution and method of the current invention and is explained in more detail below.

Currently, scorpion venom solutions are not available in a polarized liquid form. Thus, there is a need in the art for a polarized blue scorpion venom solution and a method for making polarized blue scorpion venom solution.

As discussed above, blue scorpion venom provides benefits to the human body through apoptosis. Apoptosis is a biological mechanism through which cytotoxicity takes place. Apoptosis diminishes unhealthy inflammatory response, improves efficacy of chemotherapy, supports growth of healthy cellular tissue, and is essential to the body's natural ability to destroy cancerous tumors.

The process of apoptosis a major focus of research and the development of new pharmaceutical drugs for the treatment of: cancer; HIV; arthritis; multiple Sclerosis; Alzheimer's Disease; a wide range of other auto-immune conditions; and supporting appropriate immune system response to organ transplants.

Because apoptosis is the primary mechanism by which blue scorpion venom relieves pain, improves immune-system response, treats cancer, prevents cancer, improves quality of sleep, reduces inflammation, and minimizes negative biological response to chemotherapy and radiation treatment, an expanded understanding of apoptosis is required. The role of cellular suicide in the formation of embryonic cells has been recognized for a great deal of time, but what was not understood was the crucial role cellular suicide plays in healthy biological function. The differences between cellular suicide and necrosis are well documented. Necrosis occurs when a cell becomes acutely injured and ruptures, causing inflammatory cells to rush in to clear away the debris. Programmed cell suicide, in contrast, is clean, quick, and involves a predictable sequence of structural changes that cause a cell to shrink and then be rapidly digested by neighboring cells. This programmed cell suicide process is called apoptosis.

Additionally, research has been done that shows that apoptosis is genetically controlled. Furthermore, the link between apoptosis and cancer is well established.

Over the last 20 years, using emerging technologies, scientists have confirmed that apoptosis plays a central role within developing organisms by shaping the neural and immune systems and molding tissue specificity. They also demonstrated that apoptosis helps to establish a natural balance between cell death and cell renewal in mature animals by destroying excess, damaged, or abnormal cells. Mounting evidence indicates that the acquired ability to resist apoptosis is a hallmark of most, and perhaps all, types of cancer. As scientists learn more about how apoptosis is thwarted by cancer, they are also gaining a greater understanding of why many tumors are resistant to the cellular suicide-inducing effects of radiation and chemotherapy. Researchers are exploring how apoptosis is regulated and how it can be selectively triggered, through tailored treatments, to induce suicide in cancer cells while leaving healthy cells alone.

To better understand apoptosis, necrosis must also be understood. Cells that are damaged by injury, such as by mechanical damage or exposure to toxic chemicals, undergo a characteristic series of changes, including: they (and their organelles, like mitochondria) swell (because the ability of the plasma membrane to control the passage of ions and water is disrupted); and the cell contents leak out, leading to inflammation of surrounding tissues.

By contrast cells that are induced to commit suicide (apoptosis): shrink; develop bubble-like blebs on their surface; have the chromatin (DNA and protein) in their nucleus degraded; have their mitochondria break down with the release of cytochrome c; break into small, membrane-wrapped, fragments; the phospholipid phosphatidylserine, which is normally hidden within the plasma membrane, is exposed on the surface; the cell fragments are bound by receptors on phagocytic cells like macrophages and dendritic cells, which then engulf the cell fragments; and the phagocytic cells secrete cytokines that inhibit inflammation (e.g., IL-10 and TGF-β). The line of events in death by suicide is so orderly that the process is often called programmed cellular death.

There are two different reasons why cells typically commit suicide. First, programmed cell death is as needed for proper development as mitosis is. For example: the resorption of the tadpole tail at the time of its metamorphosis into a frog occurs by apoptosis; the formation of the fingers and toes of the fetus requires the removal, by apoptosis, of the tissue between them; the sloughing off of the inner lining of the uterus (the endometrium) at the start of menstruation occurs by apoptosis; and the formation of the proper connections (synapses) between neurons in the brain requires that surplus cells be eliminated by apoptosis. Second, programmed cell death is needed to destroy cells that represent a threat to the integrity of the organism. For example: cells infected with viruses. Indeed, one of the methods by which cytotoxic T lymphocytes (CTLs) kill virus-infected cells is by inducing apoptosis. Moreover, as cell-mediated immune responses wane, the effector cells must be removed to prevent them from attacking body constituents. CTLs induce apoptosis in each other and even in themselves. Defects in the apoptotic machinery are associated with autoimmune diseases such as lupus erythematosus and rheumatoid arthritis.

Cells with DNA damage. Damage to its genome can cause a cell to disrupt proper embryonic development leading to birth defects or become cancerous. Cells respond to DNA damage by increasing their production of a protein called p53. p53 is a potent inducer of apoptosis. Mutations in the p53 gene frequently cause a defective protein to be produced. These mutated p53 genes are often found in cancer cells and these cancer cells represent a lethal threat to the organism if permitted to live.

Cancer cells. Radiation and chemicals used in cancer therapy induce apoptosis in some types of cancer cells. Radiation and chemotherapy cause apoptosis by withdrawing positive signals; that is, signals needed for continued survival, or by sending negative signals.

Withdrawal of positive signals. The continued survival of most cells requires that they receive continuous stimulation from other cells and, for many, continued adhesion to the surface on which they are growing. Some examples of positive signals: growth factors for neurons; and Interleukin-2 (IL-2), an essential factor for the mitosis of lymphocytes.

Receipt of negative signals cause: increased levels of oxidants within the cell; damage to DNA by these oxidants or other agents like ultraviolet light, x-rays, and chemotherapeutic drugs; accumulation of proteins that failed to fold properly into their proper tertiary structure; molecules that bind to specific receptors on the cell surface and signal the cell to begin the apoptosis program. These death activators include: tumor necrosis factor-alpha (TNF-α) that binds to the TNF receptor; lymphotoxin (also known as TNF-β) that also binds to the TNF receptor; and Fas ligand (FasL), a molecule that binds to a cell-surface receptor named Fas (also called CD95).

The Mechanisms of Apoptosis. There are 3 different mechanisms by which a cell commits suicide by apoptosis. The first is generated by signals arising within the cell (internal signals). The second is triggered by death activators binding to receptors at the cell surface, such as TNF-α, Lymphotoxin, and Fas ligand (FasL). The third is reactive oxygen.

Apoptosis triggered by internal signals involves the intrinsic or mitochondrial pathway. In a healthy cell, the outer membranes of its mitochondria display the protein Bcl-2 on their surface. Internal damage to the cell (e.g., from a reactive oxygen species) causes Bcl-2 to activate a related protein, Bax, which punches holes in the outer mitochondrial membrane, causing cytochrome c to leak out. The released cytochrome c binds to the protein Apaf-1 ("apoptotic protease activating factor-1"). Using the energy provided by ATP, these complexes aggregate to form apoptosomes. The apoptosomes bind to and activate caspase-9. Caspase-9 is one of a family of over a dozen caspases. They are all proteases. They get their name because they cleave proteins, mostly each other, at aspartic acid (Asp) residues. Caspase-9 cleaves and, in so doing, activates other caspases (caspase-3 and -7). The activation of these "executioner" caspases creates an expanding cascade of proteolytic activity (rather like that in blood clotting and complement activation) which leads to digestion of structural proteins in the cytoplasms, degradation of chromosomal DNA, and phagocytosis of the cell.

Apoptosis triggered by external signals involves the extrinsic or death receptor pathway. Fas and the TNF receptor are integral membrane proteins with their receptor domains exposed at the surface of the cell, binding of the complementary death activator (FasL and TNF respectively) transmits a signal to the cytoplasm that leads to activation of caspase 8. Vaspase 8 (like caspase 9) initiates a cascade of caspase activation leading to phagocytosis of the cell.

When cytotoxic T cells recognize (bind to) their target, they produce more FasL at their surface. This binds with the Fas on the surface of the target cell leading to its death by apoptosis.

Apoptosis-inducing factor (AIF) is a protein that is normally located in the inter-membrane space of mitochondria. When the cell receives a signal telling it that it is time to die, AIF is released from the mitochondria (like the release of cytochrome c in the first pathway); migrates into the nucleus; binds to DNA, which triggers the destruction of the DNA and cell death.

Apoptosis and Cancer. Some viruses associated with cancers use tricks to prevent apoptosis of the cells they have transformed. Several human papilloma viruses (HPV) have been implicated in causing cervical cancer. One of them produces a protein (E6) that binds and inactivates the apoptosis promoter p53. Epstein-Barr Virus (EBV), the cause of mononucleosis and associated with some lymphomas, produces a protein similar to Bcl-2 and produces another protein that causes the cell to increase its own production of Bcl-2. Both these actions make the cell more resistant to apoptosis (thus enabling a cancer cell to continue to proliferate). Even cancer cells produced without the participation of viruses may have tricks to avoid apoptosis. Some B-cell leukemias and lymphomas express high levels of Bcl-2, thus blocking apoptotic signals they may receive. The high levels result from a translocation of the BCL-2 gene into an enhancer region for antibody production. Melanoma (the most dangerous type of skin cancer) cells avoid apoptosis by inhibiting the expression of the gene encoding Apaf-1. Some cancer cells, especially lung and colon cancer cells, secrete elevated levels of a soluble "decoy" molecule that binds to FasL, plugging it up so it cannot bind Fas. Thus, cytotoxic T cells (CTL) cannot kill the cancer cells by the mechanism shown above. Other cancer cells express high levels of FasL, and can kill any cytotoxic T cells (CTL) that try to kill them because CTL also express Fas (but are protected from their own FasL).

Apoptosis in the Immune System. The immune response to a foreign invader involves the proliferation of lymphocytes, T and/or B cells. When their job is done, they must be removed leaving only a small population, of memory cells. This is done by apoptosis. Very rarely humans are encountered with genetic defects in apoptosis. The most common one is a mutation in the gene for Fas, but mutations in the gene for FasL or even one of the caspases are occasionally seen. In all cases, the genetic problem produces autoimmune lymphoproliferative syndrome or ALPS. The features of ALPS include: an accumulation of lymphocytes in the lymph nodes and spleen greatly enlarging them; the appearance of clones that are autoreactive, that is, attack "self" components producing such autoimmune disorders as hemolytic anemia and thrombocytopenia; and the appearance of lymphoma, a cancerous clone of lymphocytes. In most patients with ALPS, the mutation is present in the germline; that is, every cell in their body carries it. In a few cases, however, the mutation is somatic; that is, has occurred in a precursor cell in the bone marrow. These later patients are genetic mosaics, with some lymphocytes that undergo apoptosis normally and others that do not. The latter tend to out-compete the former and grow to become the major population in the lymph nodes and blood.

Apoptosis and AIDS. HIV (human immunodeficiency virus) invades CD4+ T cells, and one might assume that it this infection by HIV that causes the great dying-off of these cells. However, that appears not to the main culprit. Fewer than 1 in 100,000 CD4+ T cells in the blood of AIDS (acquired immunodeficiency syndrome) patients are actually infected with the virus any uninfected CD4+ cells. The hallmark of AIDS is the decline in the number of the patient's CD4+ T cells (normally about 1000 per microliter (µl) of blood). CD4+ T cells are responsible, directly or indirectly (as helper cells), for all immune responses. When their number declines below about 200 per µl, the patient is no longer able to mount effective immune responses and begins to suffer a series of dangerous infections. The cause of the disappearance of CD4+ T cells is clear: apoptosis. The actual mechanism is not as clear. One mechanism may be: all T cells, both infected and uninfected, express Fas; the expression of a HIV gene (called Nef) in a HIV-infected cell causes the cell to express high levels of FasL at its surface while preventing an interaction with its own Fas from causing it to self-destruct. However, when the infected T cell encounters an uninfected one (e.g. in a lymph node), the interaction of FasL with Fas on the uninfected cell kills it by apoptosis.

Apoptosis and organ transplants. For many years it has been known that certain parts of the body such as the anterior chamber of the eye and the testes have antigens that fail to elicit an immune response. This finding raises the possibility of a new way of preventing graft rejection. If at least some of the cells on a transplanted kidney, liver, heart, etc. could be made to express high levels of FasL, which might protect the graft from attack by the T cells of the host's cell-mediated immune system. If so, then the present need for treatment with immunosuppressive drugs for the rest of the transplant recipient's life would be reduced or eliminated. So far, the results in animal experiments have been mixed. Allografts engineered to express FasL have shown increased survival for kidneys but not for hearts or islets of Langerhans.

Apoptosis activation as a therapeutic strategy for cancer. Cell survival is maintained by a balance between pro-apoptotic and anti-apoptotic stimuli. Dysregulation of apoptosis can disrupt the equilibrium between cell growth and cell death and is an important step in the development of cancer. It is this understanding that has led to the investigation of therapeutic activation of apoptosis in cancer cells as a potential anticancer strategy.

The role of p53 protein in apoptosis. Chemotherapy/radiotherapy-induced and p53-mediated activation of apoptosis via the intrinsic signaling pathway. As prior research has found, the tumor suppressor protein p53 is one of many proteins that contributes to the activation of the intrinsic signaling pathway. Inactivation of this protein or elements of its attendant pathway (upstream activators and/or downstream effectors), due to mutation, is seen in as many as half of all human cancers. Because of the important role of p53 in the intrinsic apoptosis pathway, such a mutation can render tumor cells resistant to conventional radio- and chemotherapy. Current conventional therapies such as radio- and chemotherapy indirectly promote apoptosis, although this is an important endpoint of the therapeutic effect. These regimens induce apoptosis by causing DNA damage. In doing so, they stimulate apoptosis through the intrinsic pathway.

Apoptosis independent of p53. Promoting the alternative "extrinsic" apoptosis pathway, which operates independently of p53, or augmenting downstream elements of the intrinsic apoptosis pathway, may have the potential to induce apoptosis both in cancer cells that are responsive and in those cancer cells that have become resistant to conventional therapies.

Apoptosis and naturally occurring chemicals. It has been shown that a variety of naturally occurring chemicals trigger apoptosis in humans, including Vitamins C and D. Extensive research has also shown that curcumin, a chemical from the culinary herb turmeric, also induces apoptosis in humans. In recent years, a tremendous amount of pharmaceutical research has turned its focus to natural venoms. Venoms of any kind are particularly intensely bioactive substances. Recently, peptides taken from the poison of the cone snail (*Conus parius*) have been approved by the FDA to be used as a treatment for chronic pain. These peptides, in the right concentration, have been shown to work as effectively as morphine, but without any addictive qualities. Venom of the scorpion *Leiurus quinquestriatus*, from the Buthidae family, has had a great deal of research associated with its efficacy in treating brain cancer. A great amount of research has been done over the last 15 years regarding scorpions of the Buthidae family and it has been shown, to varying degrees, that the venom from this family produces apoptosis in humans when administered in appropriate concentrations.

This research led to the present invention, a polarized dilute scorpion venom solution, a method for making a polarized dilute scorpion venom solution, and a method for administering dilute scorpion venom solution. The polarized dilute scorpion venom solution relieves pain, improves immune-system response, treats cancer, prevents cancer, improves quality of sleep, reduces inflammation, and minimizes negative biological response to chemotherapy and radiation treatment.

BRIEF SUMMARY OF THE INVENTION

To minimize the limitations in the prior art, and to minimize other limitations that will become apparent upon reading and understanding the present specification, the present invention discloses a polarized dilute blue scorpion venom solution.

One embodiment of this invention is a solution, comprising: a blue scorpion venom; and a distilled water; wherein the solution is polarized. The solution also relieves pain, reduces inflammation, boosts the immunity response, prevents cancer and tumor growth, treats cancer, reduces tumor growth, minimizes negative biological response to chemotherapy and radiation treatment, increases appetite and body mass during chemotherapy and radiation treatment, and improves the quality of sleep.

Another embodiment of the invention is a method of magnetically polarizing blue scorpion venom, comprising the steps of: diluting a blue scorpion venom in a distilled water to create a dilute scorpion venom solution; circulating the dilute scorpion venom solution through an one or more plastic tubes; placing a series of flat magnets along the one or more plastic tubes in pairs and on an one or more opposite sides of the one or more plastic tubes, wherein the series of flat magnets are aligned so that an one or more negative poles and an one or more positive poles of the series of flat magnets mirror one another such that the series of flat magnets repel one another; compressing the series of flat magnets together with a clamp so that the series of flat magnets remain in place, wherein the series of flat magnets that are compressed together also compress the one or more plastic tubes such that the dilute scorpion venom solution is forced to flow through the one or more plastic tubes in close proximity to the series of flat magnets; and repeating the circulation step until the dilute scorpion venom solution is polarized. The polarized scorpion venom solution treats pain, reduces inflammation, prevents cancer and tumor growth, and treats cancer.

Another embodiment of the invention is a method of administering a blue scorpion venom, comprising the steps of: diluting the blue scorpion venom; polarizing the dilute blue scorpion venom; and administering the polarized dilute blue scorpion venom to humans. The blue scorpion venom is administered to humans orally. The blue scorpion venom reduces pain, reduces inflammation, prevents and treats cancer, boosts the immune system of a humans, and boosts the level of available energy.

An object of the present invention is to provide a scorpion venom solution that relieves pain, reduces inflammation, boosts the immunity response, prevents cancer and tumor growth, treats cancer, reduces tumor growth, minimizes negative biological response to chemotherapy and radiation treatment, increases appetite and body mass during chemotherapy and radiation treatment, and improves the quality of sleep.

Another object of the present invention is to provide a method of polarizing a blue scorpion venom solution that relieves pain, reduces inflammation, boosts the immunity response, prevents cancer and tumor growth, treats cancer, reduces tumor growth, minimizes negative biological response to chemotherapy and radiation treatment, increases appetite and body mass during chemotherapy and radiation treatment, and improves the quality of sleep.

Another object of the present invention is to provide a polarized dilute blue scorpion venom solution that is safe, effective, easy to make, and easy to administer.

Another object of the present invention is to provide a polarized dilute blue scorpion venom solution that may be used by a wide variety of people regardless of their body size or individual characteristics.

Discussion on Safety. Dilute blue scorpion venom solution has been shown to be safe in numerous clinical trials. A fundamental different between necrosis and apoptosis is that in scientific studies necrosis has always been shown to produce an inflammatory response. Apoptosis does not produce an inflammatory response. In twenty-eight years of study of blue scorpion venom, it has never been shown to produce an inflammatory response in adequate dosages. However, blue scorpion venom has been shown to slow or reverse the growth of tumors with an 89.5% success rate. From this it may be concluded that blue scorpion venom produces apoptosis in cancer patients. Blue scorpion venom is a land-breaking innovation in the fight against cancer. The primary reason for this conclusion is that blue scorpion venom has undergone an eight year Third Stage clinical trial involving 8,302 people, which showed that blue scorpion venom has no negative side effects, yet has an 89.5% success rate with cancer patients. This is unprecedented is the field of oncology. In addition, because blue scorpion venom has shown extremely potent analgesic and anti-inflammatory effects. Blue scorpion venom works as an extraordinary compliment to traditional therapy including: surgery; chemotherapy; radiation; hormone therapy; and other conventional treatments.

The following is a summary of the eight year, 8,302 patient Third Stage Clinical Trial. The information below is a summary of laboratory study commissioned by the Cuban pharmacological company, Labiofirm, presented by authors Alexis Diaz, Ph.D., Luis Morier, Yamira Caballero Lorenzo, Sergio Luis Yzquierdo Silverio, Sergio Luis Maestre Mesa, Ph.D.

Pre-clinical and clinical trials have shown that blue scorpion venom is safe and has no toxic side effects. High concentrations of blue scorpion venom were administered in pre-clinical trials repeatedly over an extended period. Even with high concentrations of blue scorpion venom no negative side effects were observed. During these pre-clinical trials, scientists recorded the following clinical signs to indicate the effect of blue scorpion venom. These clinical signs include: Normal Motor Activity; Healthy Reflexes; Response to Pain; Salivation; Sedation/Healthy Sleep; Responsiveness; Condition/Appearance of the Skin; Condition/Appearance of Mucous Membranes; Condition/Appearance of the Eyes; and Condition/Health of Internal Organs. Over the course of this study, all participants remained healthy. They maintained healthy weight and levels of activity. No harm was indicated to any of the internal organs of those who participated in the study and all were in healthy working order. In summary, it was scientifically determined that blue scorpion venom has no toxic side effects.

Other features and advantages are inherent in the polarized dilute blue scorpion venom solution claimed and disclosed will become apparent to those skilled in the art from the following detailed description and its accompanying drawings.

DETAILED DESCRIPTIONS OF THE INVENTION

Figure 1:
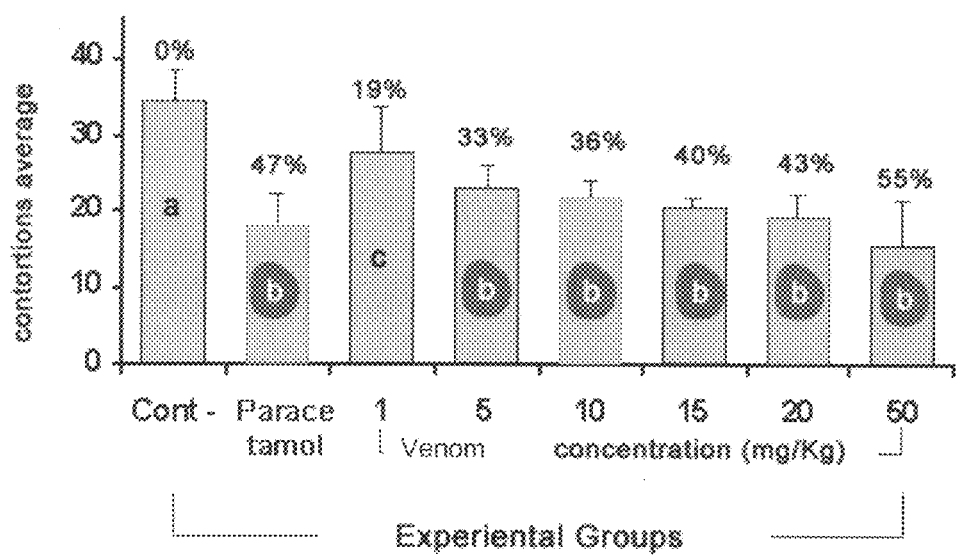
FIG. 1 is an illustration of the results of a study that shows the effectiveness of blue scorpion venom as a pain killer.
Figure 2:
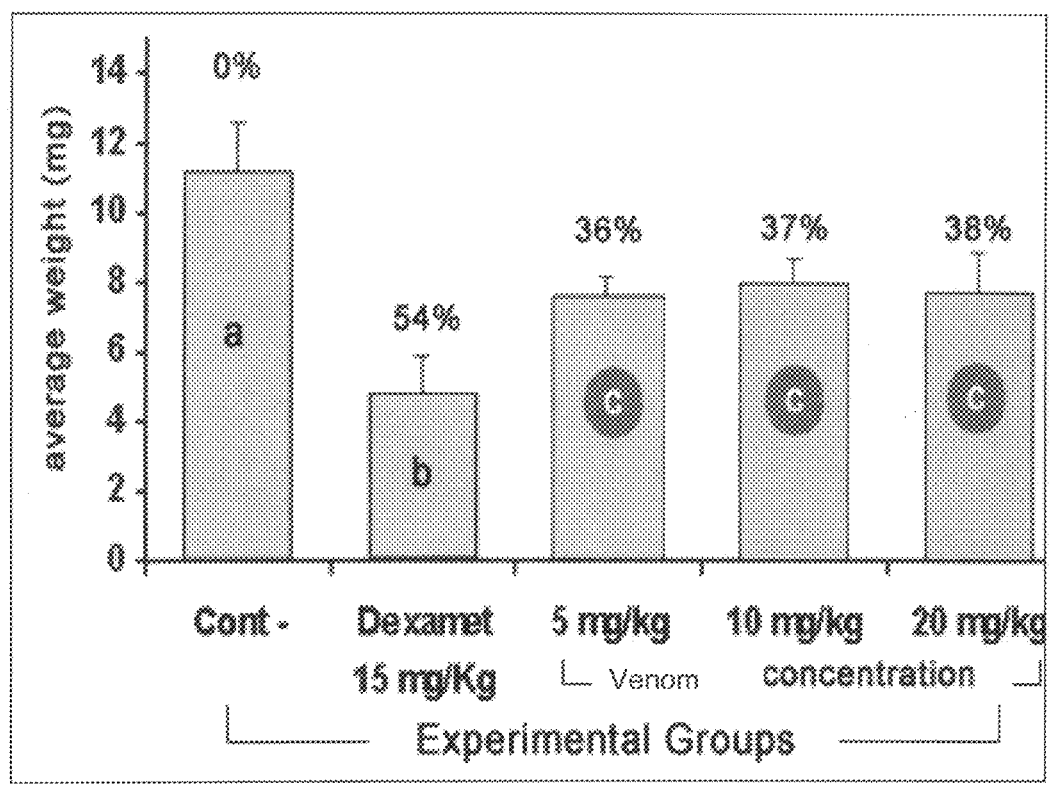
FIG. 2 is an illustration of the results of a study that shows the effectiveness of blue scorpion venom as an inflammation reducer.

In the following detailed description of the preferred embodiment, reference is made to the accompanying drawings that form a part hereof, and in which is shown, by way of illustration, a specific embodiment in which the invention may be practiced. It is to be understood that other embodiments may be utilized and structural changes may be made without departing from the scope of the present invention.

In the following detailed description of various embodiments of the invention, numerous specific details are set forth in order to provide a thorough understanding of various aspects of one or more embodiments of the invention. However, one or more embodiments of the invention may be practiced without these specific details. In other instances, well-known methods, procedures, and/or components have not been described in detail so as not to unnecessarily obscure aspects of embodiments of the invention.

This invention discloses a polarized dilute blue scorpion venom solution, a method for making polarized dilute blue scorpion venom solution, and a method to administer polarized dilute blue scorpion venom solution to humans. As preferred, the active ingredient in the solution is the venom of *Rhopalurus junceus* (blue scorpion). The venom is preferably extracted from a bioterium of scorpions (*Rhopalurus junceus*—blue scorpion) in order to obtain the quantity of venom necessary to produce an organic, natural, and health supplement. The bioterium preferably houses at least ten thousand (10,000) blue scorpions.

Scorpion acquisition and involved professional safety should be considered, and the preferred method is disclosed below. In addition, the captivity, handling, and feeding techniques are described, as well as the method and equipment used for venom extraction. Because scorpions are fragile and somewhat dangerous, a safe methodology to handle the animals is preferred. Scorpion acquisition is preferably done by professionals with over 15 years experience in the acquisition, study, and maintenance of scorpions in bioteriums. Regular and appropriate feeding of the animals should be maintained, along with regular cleaning of cages. Consequently, the survival of the animals preferably exceeds multiple venom extractions. Controlled handling and more appropriate maintenance of the scorpions will allow for higher survival rates, and better yields of venom.

Scorpion acquisition, preferably, starts in Haiti. The blue scorpions should then be imported to the bioterium. This first generation of scorpions is preferably transported in protected units so that they will be unable to escape into the environment. Animal quarantine will be done by the rules and regulations as set forth by the country into which the bioterium is set up. All necessary tests indicating the health of the scorpions should be obtained through the appropriate ministries of the importing country.

Personnel safety. The bioterium staff should be issued protective rubber gloves which will be impossible for the sting of *Rhopalurus junceus* (blue scorpion) to penetrate. The staff is preferably required to wear this protective gear whenever they are in contact with the scorpions or on the grounds of the scorpion bioterium, thereby protective themselves from injury. A LD 50 value of 8.0 mg/kg has been reported for the blue scorpion species. This indicates that the blue scorpion species is not among the most venomous scorpions. This is a common scorpion in Haiti, and many people are stung each year. The only deaths that have been reported are attributable to anaphylactic shock following a hypersensitivity immune reaction. Though the sting of *Rhopalurus junceus* (blue scorpion) is non-fatal and rarely elicits a severe physical reaction, in case of a highly unusual allergic reaction to the bite, medication and antidote are preferably present and available at the scorpion bioterium at all times.

Environmental Safety. The acquired blue scorpions should be imported utilizing sealed, perforated boxes which will allow the scorpions sufficient air without providing any opportunity for escape. Once transported to the bioterium, the scorpions should be carefully transferred individually into cages, preferably 50 centimeters wide by 75 centimeters long by 40 centimeters high in size, and made of light colored polyethylene for easy visual monitoring. However, the cages can be of any size, material or color without deviating from the scope of this invention. The corners of the boxes will be covered with plastic adhesive tape. This tape will prevent any scorpions from escaping. These cages will be stored a significant distance from any exits to the building so that in the highly likely case that a scorpion should leave its cage, the bioterium technicians will be able to see the animal before it has the possibility of escaping. Finally, each cage will be numbered with a count of the scorpions for that cage. This count will be verified at the beginning and end of each day to ensure that the correct number of scorpions is encaged and that there are no escaped animals.

Animal Safety. From acquisition to transportation to deposition in the bioterium, every effort should be made to ensure the safety and minimized stress of the animals. This is important because a stressed scorpion may not deliver as high a quality of venom. Great care should be made to ensure that excessive movement does not occur of the travel containers holding the scorpions. Once deposited in the bioterium, the scorpions should be regularly monitored for health and levels of stress. Their cages should include natural items such as earth, sand, and bricks to better replicate a natural environment. Cages should be regularly cleaned and the scorpions fed a nutritious, all-natural diet.

Bioterium of scorpions preferably consists of one area covering twelve (12) square meters, and is preferably designed to keep spiders, scorpions, and insects in place and safe. The room should be equipped with several windows that provide natural ventilation; heaters should be turned on during colder months to maintain the temperature between 23-25° C.

The animals, which arrive in the bioterium, are identified and selected: adult specimens, ready for venom extraction, are accommodated in appropriate cages according to first, second, third extraction, and so on. All the activities should be supervised and controlled by a professional in order to obtain satisfactory results. Birth of young in the captivity is common. If there is a possibility of raising them, it is necessary to isolate the females and their progeny, and then the young from the mother.

The animals used in the venom production should be kept in different cages. In order to maintain a productivity control, the animals from different extractions should never be mixed. Preferably the cages allow for easy visual monitoring. Typically, commercially available boxes have rough corners that allow animals to escape. To avoid this, the corners are covered with plastic adhesive tape. The cage floor is preferably covered with a plate of waved cardboard to offer comfort to the animals and avoid unnecessary stress. Layers of waved cardboard that are overlaid and folded in accordion shape, increase the surface area of the habitat and avoid excessive contact among the animals, preventing frequent cannibalism. Cardboard offers appropriate protection since the scorpions show a high night activity. Further, cardboard is an extremely light material, avoiding wound to the animals during handling. It is also cheap and easy to find in the market. Water is supplied in plastic bowls (one in each cage), containing wet cotton. The cages are placed on iron shelves and covered with net lids framed with wood; they should be labeled accordingly. A control file should be kept beside each cage and data such as entrance date, feeding, extraction, and death are registered.

Maintenance is preferably performed weekly, and includes change of cotton and cardboard, removal of dead animals and wash of each one of the boxes with water and neutral soap. Daily handling should be avoided in order to decreasing animal stress. Other substrates such as earth, sand, bricks, and roof tile may also be used to imitate the natural habitat of the blue scorpion.

Feeding. The bioterium should be stocked with several kinds of insects to feed all the animals in the bioterium. Food is offered to the scorpions once a week, after venom extraction, preferably consisting of *Gryllus* sp., *Periplaneta americana*, or *Pycnocellus* sp. (common roaches and crickets). The insects are kept in the cages for two days and then the cleaning is performed, removing all animals, washing the cages with water and neutral soap, and changing cotton and cardboard. Every week, specimens from two or three cages are fed according to the food availability, assuring that each cage receives food at least every forty (40) to fifty (50) days a year. The quantity of food is calculated according to the quantity of scorpions in each cage: preferably a roach for every two animals, or an adult cricket for every animal.

Venom extraction is preferably performed every month. The scorpions should be milked for their venom on a monthly basis, preferably, by highly trained staff. The venom is extracted by a mild electro-shock placed briefly on the tail of the scorpion which encourages the scorpion to release its venom. This shock causes no physical damage to the scorpion, nor does it shorten the life span of the scorpion. The venom is then collected into a small cup and placed in refrigerated storage to maintain the quality of the venom. Food is given a week after venom extraction in order to allow time for the animals to recover from any stress associated with the venom extraction. If they are fed before the extraction, the quantity of venom produced can be affected.

Storage and transportation of the venom. Once extracted, the venom is preferably kept in a locked refrigeration unit. Preferably, the venom is regularly transported from the bioterium to a production facility. If the production facility is in the United States it should be an FDA licensed production facility. When transported, the venom is preferably maintained in a temperature controlled, double-sealed container for added safety and to maintain venom quality.

Production of the dilute scorpion venom solution.

As noted above, the first stage of production of the dilute scorpion venom solution of the present invention is extraction. Individual "crops" of scorpions are extracted every 30 days. These crops are kept separated from one another, but are given the same diet. This consistency in diet, timing of extraction, and population control is intended to support consistency of concentration of venom per each extraction.

Preferably, a one hundred milliliters (100 ml) glass container. The container can be empty, as preferred, or filled with of medical distilled water, which is used for extraction. Using electrical stimulation of each scorpion's tail, drops of scorpion venom will be captured in this 100 ml glass container. Into each 100 ml container, approximately two hundred (200) drops of venom are extracted with an average of 2.55 drops from each scorpion.

The second step is transportation. Once extraction is completed, the container is sealed and placed into a refrigerated environment. The container should be kept in that refrigerated environment for thirty minutes until the venom reaches a maximum of twelve degrees centigrade (12 C (52 F)). At that time, the container should be packed into a refrigerated compartment which keeps an even temperature range between 12 and 14 C (52-58 F) for 48 hours. These times and temperatures are preferred, but a wide variety of times and temperatures are acceptable without deviating from the scope of the invention.

The third step is receiving. The manufacturing (preferably pharmaceutical) laboratory receives the concentrated venom solution. This concentrate should be brought to the laboratory facility. This concentrate should be received in individual containers ranging in size from 100 ml to 500 ml.

The fourth step is initial storage. The laboratory must immediately refrigerate the concentrate. As noted above, the concentrate is preferably received by the laboratory in a refrigerated container. Concentrate is preferably refrigerated and maintained at a range between 12 to 14 C (52 F-58 F). The concentrate degrades at an accelerated rate when exposed to bright light; as such, this refrigerated storage environment should be protected from light and without internal illumination.

The fifth step is filtration. Scorpion venom is a complex mixture of salts, small molecules, peptides, and other proteins. The laboratory should filter the venom using glass fiber membrane filter that is preferably 0.80 µm, 25 mm, 1 pk/50 pcs. This ensures the sterilization and purification of the venom. The venom from a crop of scorpions is extracted and filtered into a single, sterilized glass container.

The sixth step is bulk manufacturing. After filtration, the venom is combined with chilled, medical-quality distilled water to achieve a specifically maintained concentration within a sterilized environment. A bulk version of the product is transferred into a sealed, sterilized bulk container and the container then transferred into to a refrigerated environment.

Determining the concentration. Typically, the dilute blue scorpion venom solution contains 0.0003 ml of venom per 0.9997 ml of distilled water (totaling 1 ml of prepared dilute solution) for treatment of third and fourth stages of cancer. Concentration for treatment of baseline, first, and second stages of cancer is preferably 0.00025 ml of venom in 1 ml of prepared dilute solution.

The final bulk dilute solution is preferably stored and shipped in a dark and refrigerated environment.

The venom has tendency to separate from water when suspended in water for an extended period of time. To achieve consistent concentration of venom, the sealed bulk container is preferably agitated in a back and forth manner for no less than 30 minutes before being transferred into individual containers. During the packaging process the bulk container should be continuously agitated through stirring.

The final step of the process is packaging and bottling. The bulk product is transferred in a sterilized environment into individual one liter bottles, which should include labels, airtight seals, and opaque containers, which protect the product from degradation due to inappropriate exposure to light. The containers are pre-sterilized before being filled with the product. The process of packaging is time sensitive. Undo exposure to air and excessive temperatures will undermine the potency of the venom. As such, time is a sensitive issue with the product. Exposed to room temperature, the process cannot be extended past a few (approximately four) hours from removal from refrigeration to completion of bottling. However, if bottling is done in a highly air conditioned environment (lower than 15 C or 58 F) or if the distilled water used in production is chilled (through prior refrigeration) then the period of production from removal from refrigeration to finalized bottling can be extended. Eight (8) hours for highly chilled distilled water; twelve (12) hours for highly refrigerated environment.

Once the bottling procedure is complete, bottles of final product are to be stored in a dark, refrigerated environment maintained, as preferred, at a temperature between 12 and 14 C (52 F and 58 F) where they will wait until final shipping.

The dilute blue scorpion venom is preferably tested for bacterial contaminants, chemical contaminants, and concentration. Standard microbial and mass spectrometry tests are preferably used. If possible, no product should be shipped to a customer until the batch has undergone testing for purity.

Standard testing procedures, such as Lowry's method for determining protein concentration should be used to quantitatively evaluate the dilute solution. Other types of procedures, known in the art, may also be used. Batches should be rejected if bacterial or chemical contaminants are found, or if more than 5% of the bottles test for levels of any chemical naturally found within the venom, but at a higher or lower concentration in excess of 10% deviation from the standard concentration per standardized mass spectrometry of the venom.

Polarization of the dilute scorpion venom solution. Preferably, the dilute solution is polarized. The preferred process for polarizing blue scorpion venom is the Mikaelian Polarized Liquid Process, named after the current inventor. The first steps in the polarization process, preferably, are to circulate the dilute scorpion venom solution repeatedly through plastic tubes. Preferably the plastic tubes are one and a half (1.5) centimeters in diameter, but they can be any diameter, and can be made from any malleable, non-metallic material. The circulation is performed by one or more small pumps. The next step of the process is to place, along the pump or tubes, a series of flat magnets. Preferably these magnets are placed in pairs along the opposite sides of the tubes and are aligned so that the negative poles and positive poles of the magnets mirror one another so that the magnets repel one another. The magnets are then compressed with one or more non-metallic, preferably wooden, clamps so that the magnets remain in place. The magnets are compressed to within two millimeters of one another, also compressing the tubes so that the water must flow through a small gap between the magnets. Two millimeters is a preferred compression point, any greater or lesser compression point may be used, so long as the liquid can flow within the tube, without deviating from the scope of the invention. Preferably, the scorpion venom dilution is circulated through this tube lined with pairs of magnets for an extended period of time. The resulting polarized liquid, compared to non-polarized liquid, is absorbed far more rapidly into the human and is significantly more bio-available on a cellular level, resulting in significantly improved results.

FIG. 5, discussed below, discloses a study that showed how polarized liquid is absorbed more rapidly into the body. The efficacy of polarized liquid has been tested in small scale blind studies in which the subjects did not know whether or not they were receiving unpolarized liquid or polarized liquid. In those cases where individuals received polarized/magnetized liquid, they reported significantly improved results. The effects of this Mikaelian polarization process stays effectively within the liquid for three to four weeks before the liquid returns to a state similar to pre-polarization. The Mikaelian polarization process works through repeated exposure to fixed magnetic fields that align the magnetic poles of the molecules within the scorpion venom liquid in such a way that it forms a geometric consistency between the molecules which influences the body's ability to recognize the liquid and open molecular gates for better absorption. Typically fixed magnets are used however, electromagnets may also be used.

FIG. 1 is an illustration of the results of a study that shows the effectiveness of blue scorpion venom as a pain killer. Blue scorpion venom is a highly effective pain killer. In this study, several groups were given different amounts of blue scorpion venom. Another group was given a powerful, clinically used analgesic (paracetamol). Another group (a control group) was not given anything. As shown in FIG. 1, compared to the control group (which received no pain killer), those participants who were given paracetamol had 47% less pain. However, those given high concentrations of blue scorpion venom had 55% less pain than those who were not given any pain killers. Thus, it may be concluded that blue scorpion venom diminishes pain by 55%.

FIG. 2 is an illustration of the results of a study that shows the effectiveness of blue scorpion venom as an inflammation reducer. Blue scorpion venom, as shown in FIG. 2, relieves inflammation. In the study, scientists created three groups. One group was given an anti-inflammatory steroid, (dexamet) often given to cancer patients after chemotherapy. Another group was not given anything. A third group was orally given blue scorpion venom. All three groups had inflammation artificially induced and were then observed. The level of inflammation was recorded by weighing the participants before and after inflammation was induced. Compared to the control group that received nothing, those who received blue scorpion venom had up to 38% less inflammation. From this information, may be concluded that the blue scorpion venom solution of the present invention, significantly reduces inflammation. Additional information from other clinical trials strongly suggests that at higher dosages than were administered in pre-clinical trials, blue scorpion venom's anti-inflammatory activity is even more powerfully enhanced.

Figure 3:
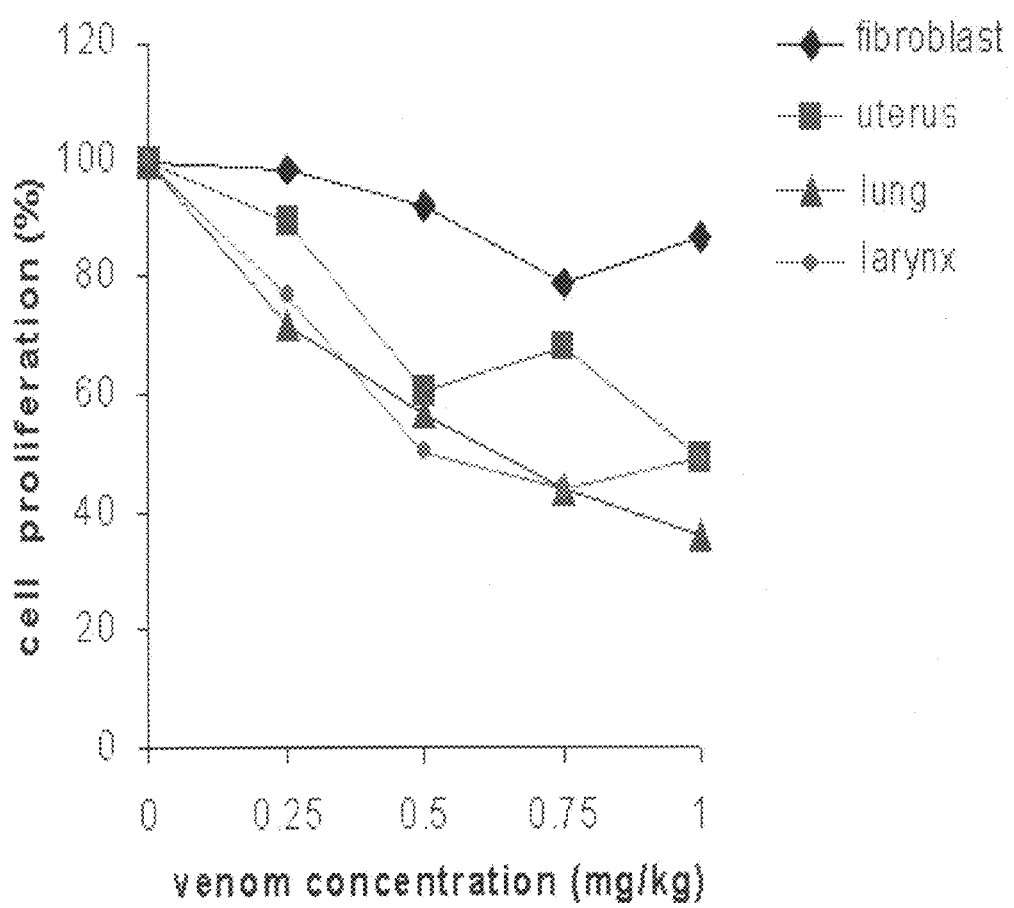
FIG. 3 is an illustration of the results of a study that shows the effectiveness of blue scorpion venom as a cancer fighter.

FIG. 3 is an illustration of the results of a study that shows the effectiveness of blue scorpion venom as a cancer fighter. As a part of the study, cancer cells from four different types of cancer were put in test tubes and then exposed to blue scorpion venom. For all types of cancer used in the study, the number of cancer cells decreased after being exposed to blue scorpion venom. One group decreased by 60% in just one week of exposure.

Figure 4:
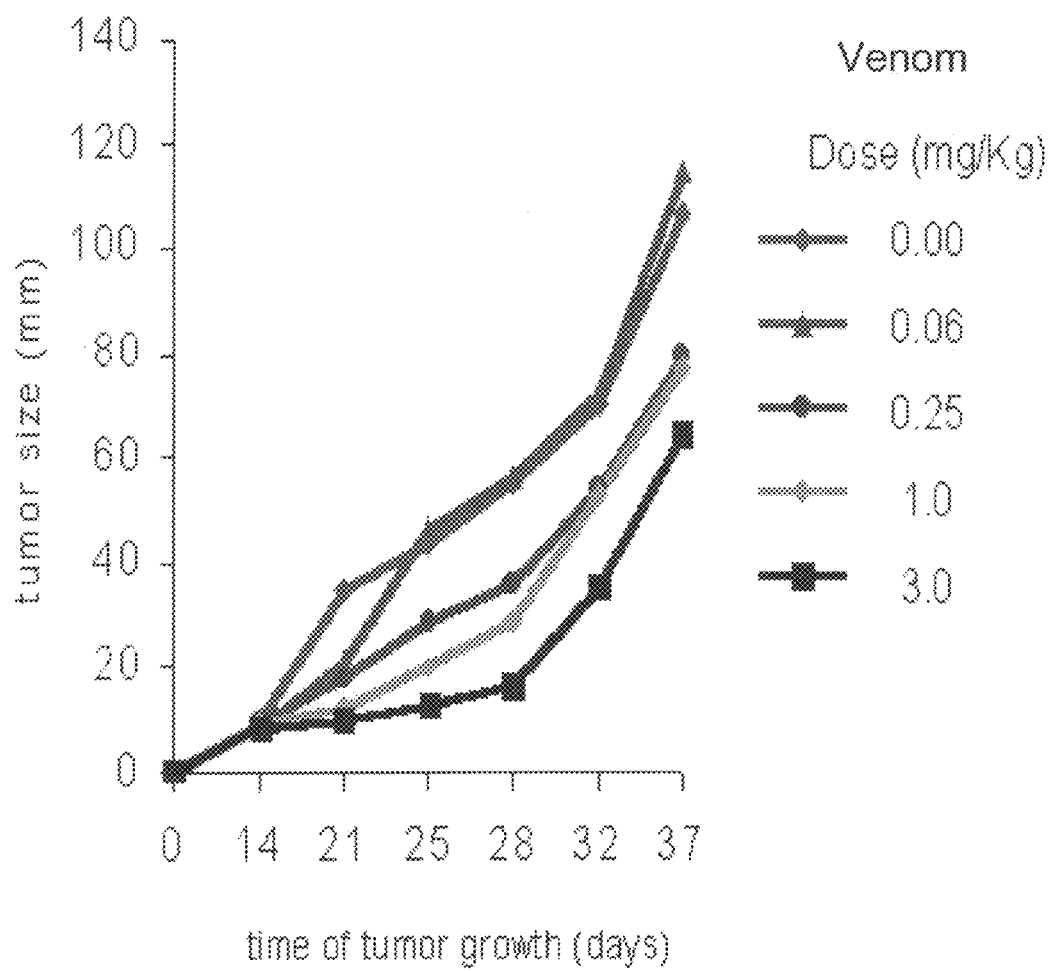
FIG. 4 is an illustration of the results of a study that shows the effectiveness of blue scorpion venom as a cancer treatment in the body.

FIG. 4 is an illustration of the results of a study that shows the effectiveness of blue scorpion venom as a cancer treatment in the body. As shown in FIG. 4, five groups had cancerous tumors. One group (the control group) was not given anything. The other four groups were given different levels of blue scorpion venom. After several weeks, the size of the tumors was assessed. The tumors in those who received high concentrations of blue scorpion venom were 45% smaller than the tumors in those which received no blue scorpion venom. From this data, it may be concluded that blue scorpion venom inhibits the growth of cancer cells in a living organism.

Figure 5:
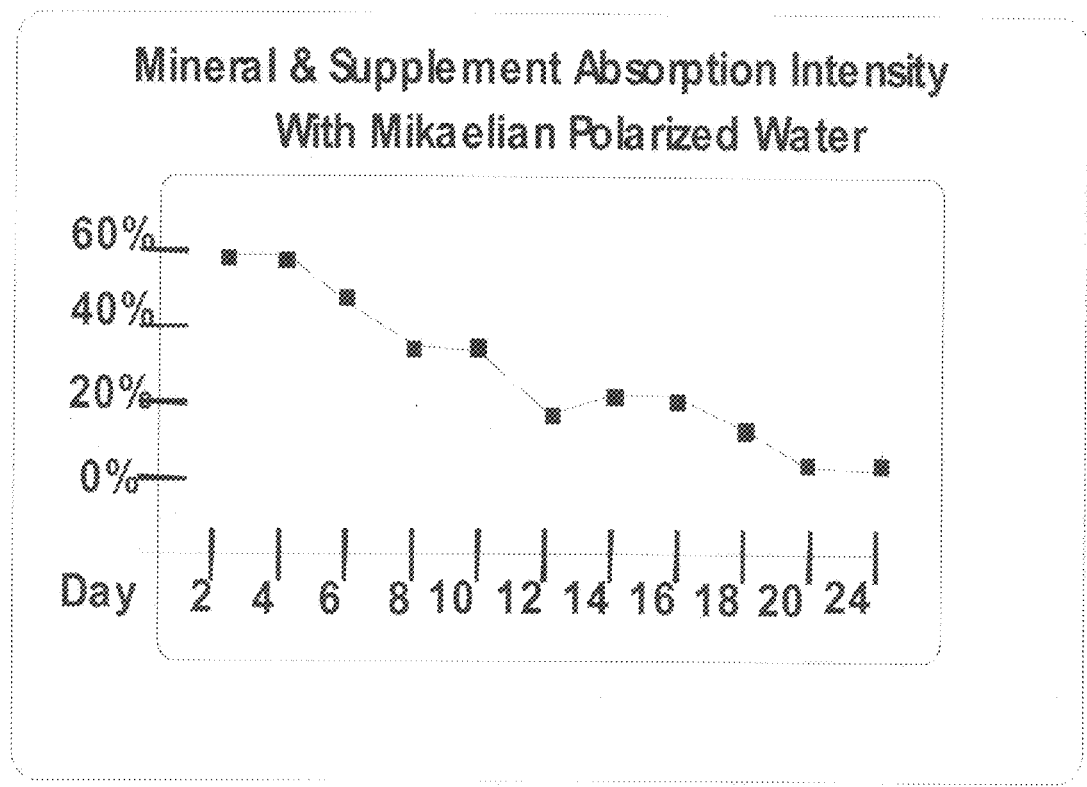
FIG. 5 is an illustration of the results of a study that shows the efficacy of the Makaelian Polarization Process.

FIG. 5 is an illustration of the results of a study that shows the efficacy of the Makaelian Polarization Process. Horizontally the graph in FIG. 5 represents 24 day testing with urine samples. Vertically the graph in FIG. 5 represents the percentage of unabsorbed minerals and supplements in urine.

An introduction to the Mikaelian Polarized Liquid (MPL) process.

The human body is composed of about 70% water and 30% solids. Normal metabolic activity can only occur when cells are at least 65% water. Water is the most important nutrient because it is responsible for so many functions and for the activation of cellular functions by other nutrients. When nutrients have reached the cells, water is necessary for the cells to function, maintain (catabolic phase) and build and repair (anabolic) phase. These two phases of cellular function are closely related to the cellular water flow or lack of its flow.

Intra-Cellular & Extra-Cellular. There are two types of water in the body, intra-cellular and extra-cellular. Extracellular is the fluid outside an individual cell while intra-cellular is the fluid found inside the cell. Both of these types of water are necessary for optimal health or wellness of every cell in the body. In order for the cells to be biologically active they must absorb water. When the cells over-hydrate it triggers an anabolic phase, one of the healing mechanisms in the body. The anabolic phase is triggered by a positive hydrogen balance, protein synthesis, or growth hormone.

Studies have been performed to test whether there is increased transportation of necessary nutrients to the cells by using a Mikaelian Polarized Liquid in order to improve the effectiveness of supplements and medications. The primary goal in this clinical study was to evaluate whether or not drinking Mikaelian Polarized Liquid with vitamins and minerals every day will increase delivery of nutrients to cells by increasing cellular hydration as a fundamental indicator of wellness. Each subject was evaluated for baseline numbers on the first day of the study. Each subject was retested on the fifteenth and the thirtieth day of the study. At each office visit we performed: analysis, height, weight, temperature, blood pressure and pulse in addition to urine, blood and saliva samples. Each subject was provided with an instruction sheet indicating how much Mikaelian Polarized Liquid to consume with each intake of vitamins and minerals. Changes in cellular hydration involve a proprietary combination of specific measurement parameters based on a mathematical formula to understand any negative deviation, with an emphasis on surface tension, specific gravity and resistivity measurements of urine, blood and/or saliva, for each subject in the study.

Conclusion of study. Upon completion of this wellness study it has been indicated that overall these test subjects showed a 27.5% increase in hydration and 58% increase in mineral absorption at a cellular level. The individual's percentages vary from 18-23.5% but all the subjects show significant increase in these wellness hydration levels per the specific method of testing cellular hydration. This study validates that a Mikaelian Polarized Liquid increases mineral and supplement absorption at the cellular level.

Technical details on the Mikaelian Polarized Liquid process.

The first step is determining the correct position of magnetic poles. It is required to have a regular compass for magnets pole determination. Position a compass on the table next to each magnet. The needle of the compass will point to the north pole of the magnet. The needle of the compass is positively charged, thus, it is attracted to the negative pole of the magnet, allowing for identification of that pole. The one of the sides of the magnet that will be used for polarization is slowly moved towards positively charged needle. If highly attracted, the compass needle indicates that it is the negative pole of the magnet. This will be used for identification. The north pole of the magnet is physically marked as a (minus) pole or negative charged. The needle of the compass is positively charged, thus, it is repulsed by the positive pole of the magnet, allowing for identification of that pole. The opposite side of the magnet that will be used for polarization is slowly moved towards the positively charged needle. If highly repulsed, the compass needle indicates that it is the negative pole of the magnet. This will be used for identification. The south (positive) pole of the magnet is physically marked in red or with plus sign to indicate that it is positively charged.

The second step is preparation of hose and magnetic sandwiches. Two wooden panels of the dimensions ten (10) centimeters in height, one (1) centimeters in width, and sixty (60) centimeters long are prepared. The panels can be of any dimension and any non-metallic material without deviating from he scope of the invention. A line of industrial strength magnets are glued to these panels using a strong epoxy resin. The magnets are affixed to the vertical center of the panel in a straight line. The negative/north/minus pole of the magnet is glued face down to the panel. The positive/south/plus pole of the magnet is face up and exposed. The magnets are lined in succession and preferably have no spacing between their edges. A plastic transparent hose two (2) meters in total length is glued to the vertical center of one of the line of magnets on the wooden panels. The hose extends approximately seventy (70) centimeters from either side of the wooden panel. The hose may be opaque and made out of any non-metallic pliable material without deviating from the scope of the invention. Four holes are drilled in each of the panels. One pair of holes is situated on end of the length of the panels; another pair of holes on the opposite end of the length of the panels. The two panels are made to face one another. They are connected by four bolts which are threaded through the four pairs of holes on either side of the panel. Threaded around each bolt is a spring to provide resistance while tightening the bolts. The bolts are tightened to a point where the wooden panels are compressed to a preferred distance no less than 3 mm in separation, compressing the plastic transparent hose in the process.

The third step of the process is connection of hose, pump, and receptacle. One end of the hose affixed to the magnetic sandwich is connected to an electric pump. The other end of the hose is deposited in a container. From that container the end of another hose of equal diameter is placed in the container. The opposite of this hose is affixed to the electric pump. The pump is preferably an electric pump, but may be any pumping or actuating device that circulates the fluid.

The fourth step is recirculation. The container is filled with distilled water or a mixture of distilled water and scorpion venom or a mixture of distilled water and nutrients or a mixture of distilled water, nutrients, and scorpion venom. The pump is turned on and the liquid is made to recirculate from the container, through the magnetic sandwich to the pump and then back to the container at a rate of approximately 190 gallons per hour. This process of recirculation is repeated at length and will vary based upon the amount of liquid being polarized. The greater the amount of liquid; the longer the process of polarization is. The lesser the amount of liquid; the shorter the process of polarization is.

Intense Magnetic Resistance (IMR). The unique element of Mikaelian Polarized Liquid is creation of Intense Magnetic Resistance (IMR) by utilizing similar poled/charged sides of magnets at very close distances. Other forms of polarization utilize magnetic attraction, while Mikaelian Polarization Process utilizes magnetic repulsion as a mechanism for polarization. Liquids flowing through Intense Magnetic Resistance (IMR) fields are subject to molecular polarization which strongly affects the geometric relationships between molecules and the electromagnetic fields surrounding those molecules in a way which is commercially significant.

Polarization enhances utilization of water and nutrients. The realignment of magnetic poles of molecules using Intense Magnetic Resistance (IMR) enhances absorption and utilization of water, nutrients, and scorpion venom on a cellular level. In particular, the cell membranes of cancer have a distinctive and excessive negative electromagnetic charge. The polarization of liquid allows for the molecules within the liquid to be utilized with extreme efficiency by cancer cells, as the positive electromagnetic poles of these molecules are thoroughly attracted to the excessive negative charge of cancer cell membranes. Specific to this application, the utilization of scorpion venom molecules leads to a rapid and efficient triggering of apoptosis (programmed cellular suicide) within cancer cells; thereby accelerating their death and inhibiting the growth of cancerous tumors.

Additional information on the cancer fighting ability of blue scorpion venom.

Several studies have shown the efficacy of blue scorpion venom in treating and fighting cancer. One of these studies, as discussed above, was a third stage clinical trial involving eight thousand three hundred and two (8,302) patients. In this study, 8,302 patients of a variety of different stages of cancer were given blue scorpion venom. A variety of cancers were studied with breast, brain, lung, prostate, and colon cancers being the most common studied. Cancers of the larynx, lung, and uterus showed the greatest benefit over the course of the study.

The researches of the trial used summaries of the clinical history of each patient issued by the doctor who tracks the patient through different medical institutions. Each patient was evaluated monthly. During the evaluation, doctors spoke with the patient or a close family member and organized their records according to the type of neoplasia (abnormal cell growth).

The conclusions of this study are staggering: no side effects occurred from taking this natural product; and 89.55% of patients experienced an improved quality of life from taking blue scorpion venom.

The Eastern Cooperative Oncology Group (ECOG) has a set up a widely recognized scale to determine the quality of life of a cancer patient enrolled in a clinical trial. Grade description: "0"=capable of carrying out a normal physical activity without restrictions; "1"=symptomatic, but not hospitalized (restriction on vigorous physical activities, but an outpatient and able to undertake light chores or those of a sedentary nature); "2"=in bed less than 50% of the time, not hospitalized, able to care for self, but unable to work more than 50% of the time when out of bed; "3" capable of personal care, but confined to a bed or chair more than 50% of the time; "4"=completely incapable of any effort, totally confined to bed; and "5"=death.

Figure 6:
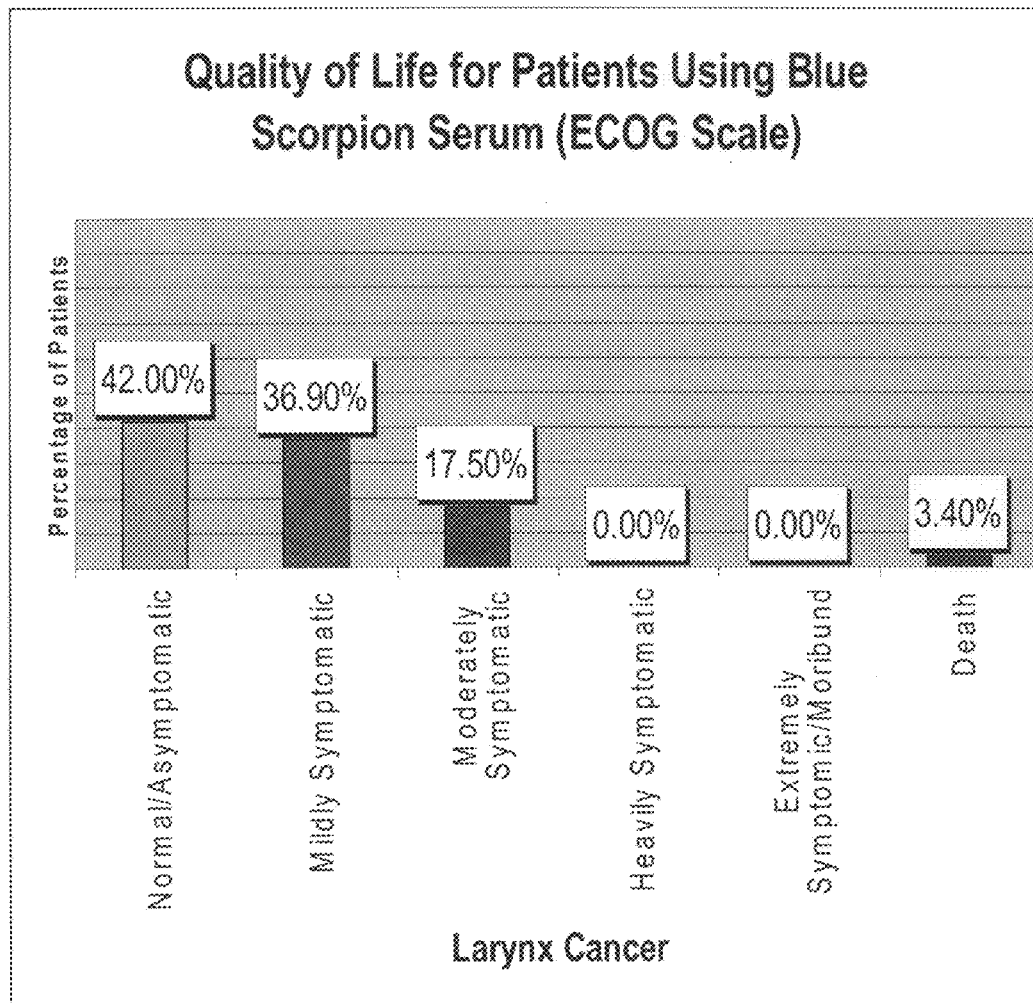
FIG. 6 is an illustration of the results of a study that shows the quality of life for larynx cancer patients that used blue scorpion venom.

FIG. 6 is an illustration of the results of a study that shows the quality of life for larynx cancer patients that used blue scorpion venom. As shown in FIG. 6, over 78% of the larynx cancer patients were asymptomatic (0 on the ECOG scale) or only mildly symptomatic (1 on the ECOG scale).

Figure 7:
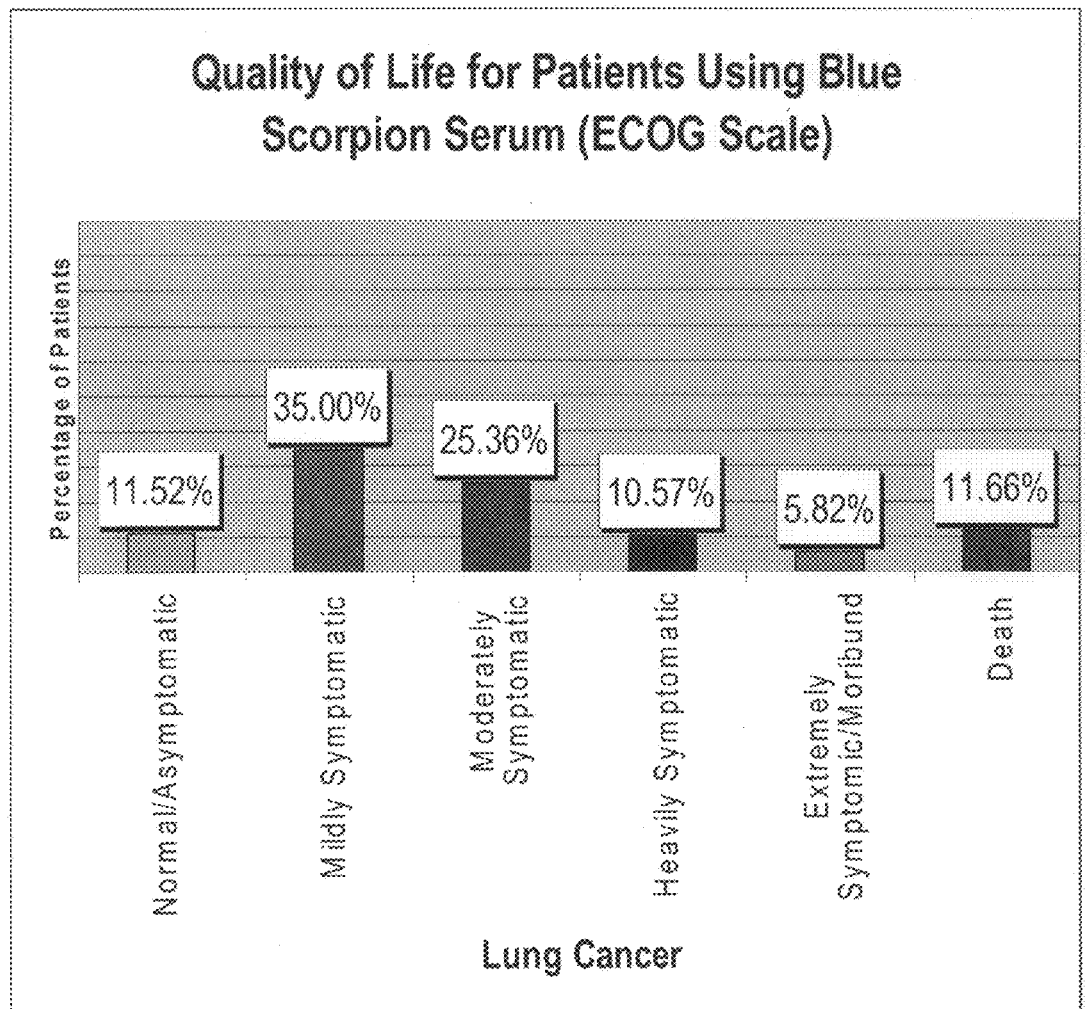
FIG. 7 is an illustration of the results of a study that shows the quality of life for lung cancer patients that used blue scorpion venom.

FIG. 7 is an illustration of the results of a study that shows the quality of life for lung cancer patients that used blue scorpion venom. As shown in FIG. 7, over 70% of the lung cancer patients were in ECOG categories 0, 1, and 2.

Figure 8:
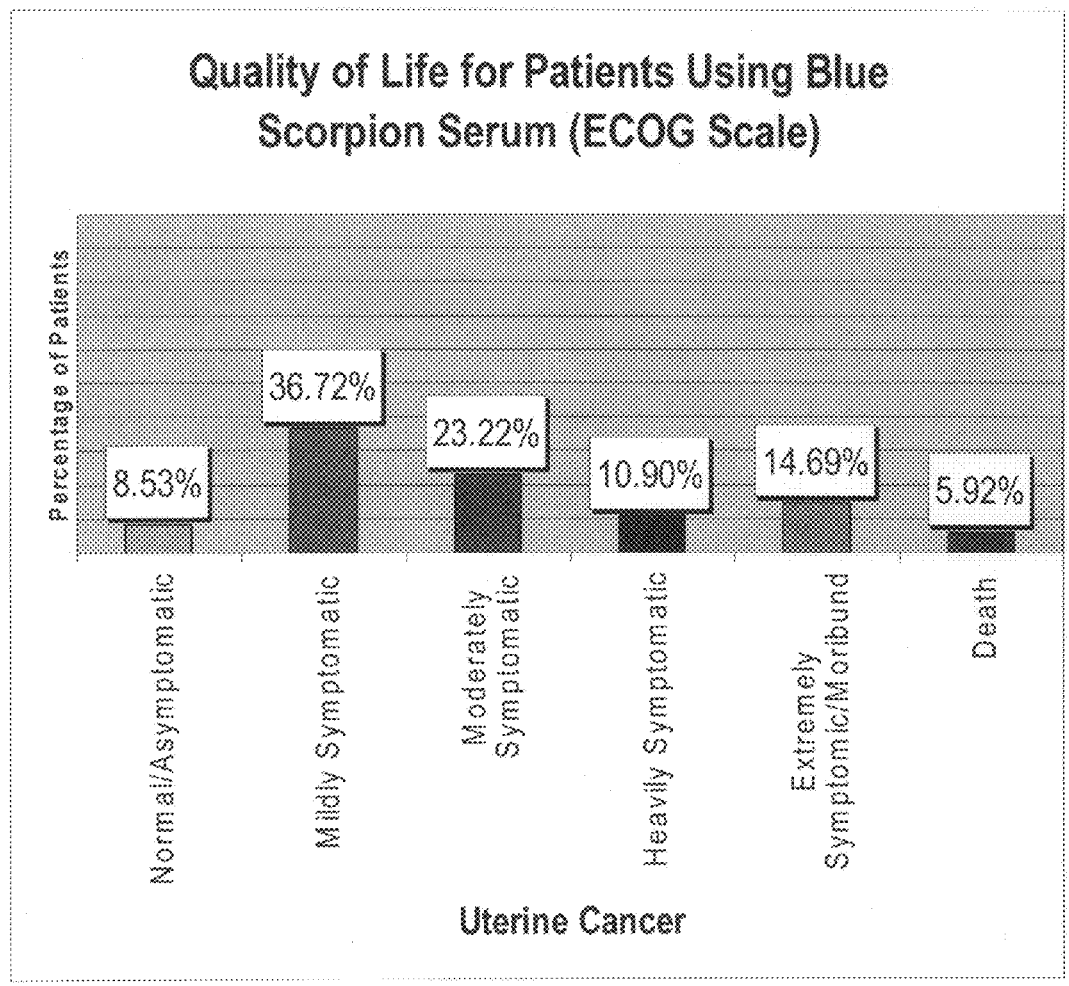
FIG. 8 is an illustration of the results of a study that shows the quality of life for uterine cancer patients that used blue scorpion venom.

FIG. 8 is an illustration of the results of a study that shows the quality of life for uterine cancer patients that used blue scorpion venom. As shown in FIG. 8, over 65% of the uterine cancer patients were in ECOG catagories 0, 1, and 2.

Figure 9:
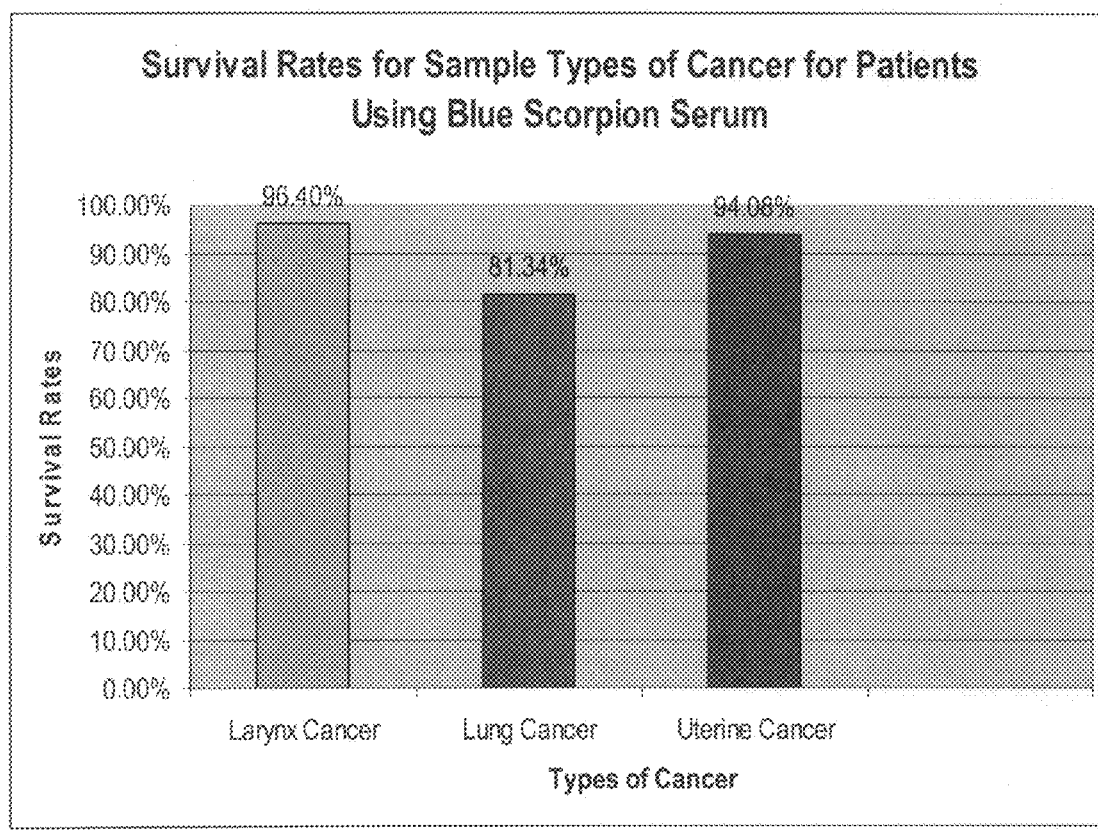
FIG. 9 is an illustration of the results of a study that shows the survival rates for the sample types of cancer for patients that used blue scorpion venom.

FIG. 9 is an illustration of the results of a study that shows the survival rates for the sample types of cancer for patients that used blue scorpion venom. As shown in FIG. 9, the survival rates of the cancer patients that used blue scorpion venom was extremely high. Over 95% of larynx cancer patients, over 80% of lung cancer patients, and over 94% of uterine cancer patients survived during the course of the study.

This study shows a substantial improvement for cancer patients that used blue scorpion venom as part of their cancer treatment regimen. Overall, 89.55% of patients in this eight-year clinical trial achieved an improvement in health and quality of life through taking blue scorpion venom, independent of what stage of cancer they were subject.

Current scientific research. Since the above mentioned clinical trial, additional independent studies, including studies conducted by the present inventor, have been conducted. This additional research validates previous results achieved by past research and the clinical trial discussed above. Although blue scorpion venom is clearly effective, not all people benefit equally from using blue scorpion venom. Some individuals immediately get well, whereas others show no signs of improvement. The additional research has developed several criteria to systemize all possible aspects which influence the effectiveness of blue scorpion venom. These factors are the result of empirical studies, and they lead to the following conclusions as in which patients blue scorpion venom tends to have greater benefit.

Current research has found that, independent of stage of cancer, it is of greater benefit to begin using blue scorpion venom as soon as is possible. Delaying onset of starting blue scorpion venom has not been shown to be beneficial.

Metastasis. Blue scorpion venom has shown the greatest benefit for those whose metastasis has not expanded to include (and heavily compromise the function of) major vital organs. Blue scorpion venom still shows benefit for those whose metastasis has included major vital organs; however, additional factors become significantly more important in these cases. Blue scorpion venom appears to have greater benefits to those patients whose cancer has not metastasized. Though blue scorpion venom still has shown amazing results with those patients whose cancer has metastasized, the type of metastasization will influence the degree of effectiveness of blue scorpion venom.

Additional complicating health conditions. Independent of whether a patient's cancer has metastasized, those patients who do not have additional chronic health issues have been shown to have more pronounced benefits. Chronic non-cancer health issues effecting vital organs (i.e. diabetes, cirrhosis, thyroid disease, etc.) tend to more greatly limit the full benefit of blue scorpion venom than chronic conditions which do not affect major vital organs. Blue scorpion venom has generally been shown to be effective even in these cases; however, once again, additional factors take on a heightened degree of importance.

Ongoing exposure to environmental toxins. The root cause of many cases of cancer is over-exposure to any of various carcinogenic toxins found in our environments. If a person's cancer is rooted in the exposure to environmental toxins, it very important for blue scorpion venom's efficacy that a person remove their self from that high-toxicity environment. Otherwise, the root cause of their cancer will continue to be supported and the benefit of Blue scorpion venom will be limited.

Genetics. Some cancer patients have a genetic (family) history of cancer. These genetically-influenced cancers are often triggered by certain environmental and stress-based factors; however, the very genetic influence of these cancers often limits the effectiveness of blue scorpion venom. Blue scorpion venom is still highly beneficial in these cases, but additional conditions need to be addressed. In addition, for those who are highly genetically susceptible to the development of cancer, blue scorpion venom has shown great promise as a preventative measure.

Psychological/environmental stress. Research has found that clients under significant amounts of psychological and/or environmental stress tend to have greater challenges with their recovery from cancer than those who are able to overcome their psychological stress and/or separate their self from extreme environmental stress. Blue scorpion venom has been found to more beneficial for those patients who through life choices, changes in lifestyle, and/or counseling are able to limit or overcome excessive psychological/environmental stress. Additionally, endocrinologic and immunologic rationales for a susceptibility to cancer in depressed patients have been proposed. These theories suggest that stresses, such as depression, lead to excesses of hormones including adrenal corticosteroids. It is through these corticosteroids that immunosuppression is mediated. Evidence for this in humans includes findings of increased levels of corticosteroids in depressed patients and lymphocyte suppression in bereaved patients compared to non-depressed subjects. Patients with compromised immune systems have been shown to have higher rates of cancer.

Dietary/nutritional factors. Nutrition and diet play a key role in the development of many cancers. Nutritional deficiencies and dietary imbalances (excessive saturated fat, lack of fiber, excessive chemical additives, etc.) have been shown to influence the development of cancer. It is essential for the benefit of a blue scorpion venom user that they maintain a healthy, balanced diet which is conscious of their condition. Blue scorpion venom users who continue to maintain an unhealthy, nutrient deficient diet do not benefit from Blue scorpion venom as powerfully as those who maintain a health conscious approach to nutrition and diet.

Psychological state/commitment to healing. Multiple studies have shown that individuals with an optimistic outlook towards their life and healing show better results than those who have a negative, pessimistic view towards life and the future. Though this is not always the case, still, as a general trend research has seen that those who are fully to their healing tend to have more positive results than those who have given up hope.

Additional information on how blue scorpion venom works in a patient's Body. Research suggests that blue scorpion venom has a multi-factorial anti-cancer effect. The key to Blue scorpion venom's success is it that it both directly attacks cancerous cells and triggers biological responses which are anti-cancer in nature, including apoptosis. Blue scorpion venom's has five primary biochemical actions. First, blue scorpion venom stimulates a person's immune system. Research has confirmed that in patients who have been administered blue scorpion venom, an increase in white blood cell count occurs. White blood cells are responsible for the protective function of the immune system. With all cancers, a person's immune system plays a crucial role. For many types of cancer, the responsiveness of one's immune system plays the determining role in that cancer's development. Second, blue scorpion venom inhibits angiogenesis in cancer tumors. Research confirms that a slowing or reversal of angiogenesis takes place for cancer tumors. It is essential for tumors to develop new blood vessels to feed their need for growth. Without these blood vessels, these tumors cannot expand, and frequently die off. Third, blue scorpion venom inhibits cancer cell functionality. Research shows that the venom *Leiurus quinquestriatus* of the Buthidae family of scorpions of inhibits the functionality of sodium/potassium channels in cell membranes. The blue scorpion (*Rhopalurus junceus*) is also a member of the Buthidae family. Being of same family and possessing biochemical similarities, deductive logic suggests that the venom of the blue scorpion also inhibits the functionality of sodium/potassium channels in cell membranes. All human cells require a balance of sodium and potassium ions to function properly. Without this crucial balance, the cell becomes weak and can die. This is the case with cancer cells exposed to blue scorpion venom. Fourth, blue scorpion venom produces cytotoxicity in cancer cells. Research shows that the venom *Leiurus quinquestriatus* of the Buthidae family produces apoptosis in low concentrations. The blue scorpion (*Rhopalurus junceus*) is also a member of the Buthidae family. Being of same family and possessing biochemical similarities, deductive logic suggests that the venom of the blue scorpion also produces apoptosis. This conclusion is further supported by more recent additional research, in which cancer cells exposed to blue scorpion venom in vitro experienced cytotoxicity. Apoptosis is concluded because patients administered blue scorpion venom do not experience an inflammatory response which normally occurs when necrosis takes place. Instead, patients administered blue scorpion venom experience a powerful anti-inflammatory response, further suggesting the expression of apoptosis. Fifth, blue scorpion venom produces a healthy neurological response to cancer. Research conducted and documented in the eight-year third stage clinical trials discussed above, found that patients taking blue scorpion venom consistently exhibited greater sedation, improved sleep, healthy reflexes, and improved motor skills. These responses indicate that blue scorpion venom somehow interacts with the nervous system in healthy, regulatory way.

Multiple research beginning in the 1950's have shown a correlation between extreme nervous system activity (excessive or deficient) and aggressive tumor cell proliferation. By playing a positive regulatory role with the nervous system, it is concluded that blue scorpion venom inhibits cancer cell proliferation through the support of healthy neurological responsiveness.

Importantly, blue scorpion venom produces cytotoxicity and inhibits cell functionality only with cancer cells and not with healthy normal cells. In the eight-year third stage clinical trials discussed above, patients consistently experienced anti-inflammatory responses, diminished pain, and improved health while cancerous tumors expressed diminished or reversed cell proliferation. The results of the clinical trials have by independently confirmed by additional research. Moreover, in vitro experiments also confirm that cancer cells exposed to blue scorpion venom experience cytotoxicity.

Blue scorpion venom produces cytotoxicity in cancer cells, but does not produce cytotoxicity with healthy cells for two reasons. First, cancer cells identify proteins in venom as viable nutrient. Cancer cells are known to aggressively seek out nutrients in their environment to support rapid cellular division. Blue scorpion venom is extremely rich in a variety of proteins. Cancer cells may misidentify and ingest these venom proteins far more aggressively than healthy cells, thereby creating a much higher absorption rate. Second, cancer cell potassium channels provide greater access to blue scorpion venom absorption. The structure of potassium channels on cancer cells are often distinct from those of found on healthy cells. The unique electrostatic charge of the proteins in blue scorpion venom may be particularly drawn to the potassium channels of cancer cells resulting in much more rapid absorption.

Blue scorpion venom as a cancer treatment. Research confirms that blue scorpion venom is effective in treating a wide variety of cancers including cancers of the: prostate; colon; lung; brain; digestive tract; breast; and cervix.

Blue scorpion venom and common health benefits. Research shows that patients administered blue scorpion venom frequently experience the following health benefits: improved quality of life; increased survival rate; and tumor remission lasting five or more years. 89.5% of patients who have used blue scorpion venom in their treatment have experienced these benefits. As stated above, these benefits are dependent upon stage of cancer, genetic issues, condition of vital organs, continued exposure to environmental toxicity, lifestyle choices of the patient, and other factors.

Some initial changes in the quality of life of a patient using blue scorpion venom include: minimized negative biological response to chemotherapy and radiation treatment; increased appetite, as well as a mid-term increase in body mass; improved quality of sleep; pain relief; and improved patient immune-system response.

Administration of blue scorpion venom. Blue scorpion venom is primarily administered orally. Some patients may also have blue scorpion venom administered via additional different formats. Oral is the most common form of administration. A patient may be given certain dietary restrictions to ensure the greatest effectiveness of blue scorpion venom. Nasal administration, through a nasal spray, is best for patients with cancers related to the nervous and skeletal systems. This administration also works well for patients in extreme pain. For patients with cancers specifically related to the respiratory system, an aerosol administration of blue scorpion venom has been shown to be most beneficial. For cancers related to the rectum or vaginal region, specifically administered drops, suppositories, or douches have had the best and most comfortable effect. For patients with skin or scalp cancer, a topical ointment of blue scorpion venom has been shown to be most effective.

The effectiveness of blue scorpion venom. Research concludes that in lung, liver, digestive tract (in general terms), prostate, and breast cancers there are positive clinical and laboratory responses approaching 89.5%. Clinical response, does not mean that 89.5% of patient's have been totally cured, rather this percentage of patients experience an improvement in quality of life and survival, and in some cases, a total cure of the disease.

Blue scorpion venom is uniquely effective in the fight against cancer. Blue scorpion venom: is successful in 89.5% of cancer patients; has undergone a Third Stage clinical trial involving 8,302 patients; has no negative side effects; is an effective analgesic; has significant anti-inflammatory properties; and in combinational therapy, blue scorpion venom has been used to improve the results with surgery, chemotherapy, radiation, hormone therapy, and other conventional treatments.

The following references provide details regarding studies and research of the efficacy of scorpion venom. These references are incorporated by reference herein as though set forth herein in full.

Bordier C. M., Martinez F. M. M., Salgado S. H. L., Bory P. G. H., Perry B. F., Granado M. R. et al. Composicion antitumoral. Certificado de autor de invencion 1995; #AGIK 35/56.

Castañeda Pasarón O. Toxinas animales: Acciones facilitadoras de la transmisión colinérgica. Revista Biología 2000; 14(1): 1-15.

Compton M M. A biochemical hallmark of apoptosis: internucleosomal degradation of the genome. Cancer Metastasis Rev September 1992; 11(2):105-19.

Chen, B. and Ji, Y. Antihyperalgesia effect of BmK AS, a scorpion toxin, in rat by plantar injection. Brain Res. 2002; 952 2, pp. 322-326.

De Armas L F. Escorpiones del Archipiélago Cubano. 1V. Nueva Especie de Rhopalurus (Scorpionida: Buthidae). Poeyana 1974; 136:1-12.

Dini L, Coppola S, Ruzittu M T, Ghibelli L. Multiple pathways for apoptotic nuclear fragmentation. Exp Cell Res Mar. 15, 1996; 223(2):340-7.

Guan, R. J., Wang, C. G., Wang, M. and Wang, D. C. A depressant insect toxin with a novel analgesic effect from scorpion Buthus martensii Karsch. Biochim. Biophys. Acta 2001; 1549 1, pp. 9-18.

Guan, R. J., Wang, M., Wang, D. and Wang, D. C. A new insect neurotoxin AngP1 with analgesic effect from the scorpion Buthus martensi Karsch: purification and characterization. J. Pept. Res. 2001; 58 10, pp. 27-35.

J. I. Kourie and A. A. Shorthouse. Properties of cytotoxic peptide-formed ion channels. Am J Physiol Cell Physiol 2000; 278: 1063-1087.

Liu, Y. F., Ma, R. L., Wang, S. L., Duan, Z. Y., Zhang, J. H., Wu, L. J. and Wu, C. F. Expression of an antitumor-analgesic peptide from the venom of Chinese scorpion Buthus martensi Karsch in *Escherichia coli*. Protein Expr Purif. 2003; 27 2, pp. 253-258.

Omran M A. Cytotoxic and apoptotic effects of scorpion *Leiurus quinquestriatus* venom on 293T and C2C12 eukaryotic cell lines. J Venom Anim Toxins incl Trop Dis 2003; 9(2):255-76.

Rajendra, W., Arunmozhiarasi, A., Jeyaseelan, K. Toxins in anti-nociception and anti-inflammation. Toxicon; 2004 44 1, pp 1-17.

Xiong, Y. M., Lan, Z. D., Wang, M., Liu, B., Liu, X. Q. Molecular characterization of a new insect neurotoxin with an analgesic effect on mice from the scorpion Buthus martensi Karsch. Toxicon 1999; 37 8, pp. 1165-1180.

In summary, the present invention is a polarized dilute scorpion venom solution, a method for making a polarized dilute scorpion venom solution, and a method for administering dilute scorpion venom solution. The polarized dilute scorpion venom solution relieves pain, improves immune-system response, treats cancer, prevents cancer, improves quality of sleep, reduces inflammation, and minimizes negative biological response to chemotherapy and radiation treatment.

The foregoing description of the preferred embodiment of the invention has been presented for the purposes of illustration and description. While multiple embodiments are disclosed, still other embodiments of the present invention will become apparent to those skilled in the art from the above detailed description, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive. Also, although not explicitly recited, one or more embodiments of the invention may be practiced in combination or conjunction with one another. Furthermore, the reference or non-reference to a particular embodiment of the invention shall not be interpreted to limit the scope the invention. It is intended that the scope of the invention not be limited by this detailed description, but by the claims and the equivalents to the claims that are appended hereto.

What is claimed is:

1. A method of magnetically polarizing blue scorpion venom, comprising the steps of:
    diluting a blue scorpion venom in a distilled water to create a dilute scorpion venom solution;
    circulating said dilute scorpion venom solution through an one or more plastic tubes;
    placing a series of flat magnets along said one or more plastic tubes in pairs and on an one or more opposite sides of said one or more plastic tubes, wherein said series of flat magnets are aligned so that an one or more negative poles and an one or more positive poles of said series of flat magnets mirror one another such that said series of flat magnets repel one another;
    compressing said series of flat magnets together with a clamp so that said series of flat magnets remain in place, wherein said series of flat magnets that are compressed together also compress said one or more plastic tubes such that said dilute scorpion venom solution is forced to flow through said one or more plastic tubes in close proximity to said series of flat magnets;
    recirculating said dilute scorpion venom solution is polarized.

* * * * *